US00PP36384P2

(12) United States Plant Patent
Gragg

(10) Patent No.: US PP36,384 P2
(45) Date of Patent: Jan. 14, 2025

(54) AVOCADO TREE NAMED 'Guacacado'

(50) Latin Name: ***Persea americana* Mill.**
Varietal Denomination: Guacacado

(71) Applicant: Gary Gragg, Lafayette, CA (US)

(72) Inventor: Gary Gragg, Lafayette, CA (US)

( * ) Notice: Subject to any disclaimer, the term of this patent is extended or adjusted under 35 U.S.C. 154(b) by 0 days.

(21) Appl. No.: 18/624,363

(22) Filed: Apr. 2, 2024

(51) Int. Cl.
*A01H 5/08* (2018.01)
*A01H 6/00* (2018.01)
*A01H 6/52* (2018.01)

(52) U.S. Cl.
USPC ..... Plt./200
CPC ..... *A01H 6/00* (2018.05); *A01H 6/525* (2018.05)

(58) Field of Classification Search
USPC ..... Plt./200
CPC ..... A01H 6/525; A01H 5/08
See application file for complete search history.

*Primary Examiner* — Keith O. Robinson

(57) ABSTRACT

A new distinct cultivar of *Persea americana* named 'GUACACADO' is described, characterized by exceptionally large fruit with thick, durable skin. Fruit matures from fall to spring. Trees have has a heavy fruit set in the absence of nearby pollinator trees as well is in a cold climate. Trees are observed cold hardy. The new variety is an avocado tree, suitable for home gardener and commercial use.

16 Drawing Sheets

Figure 1:
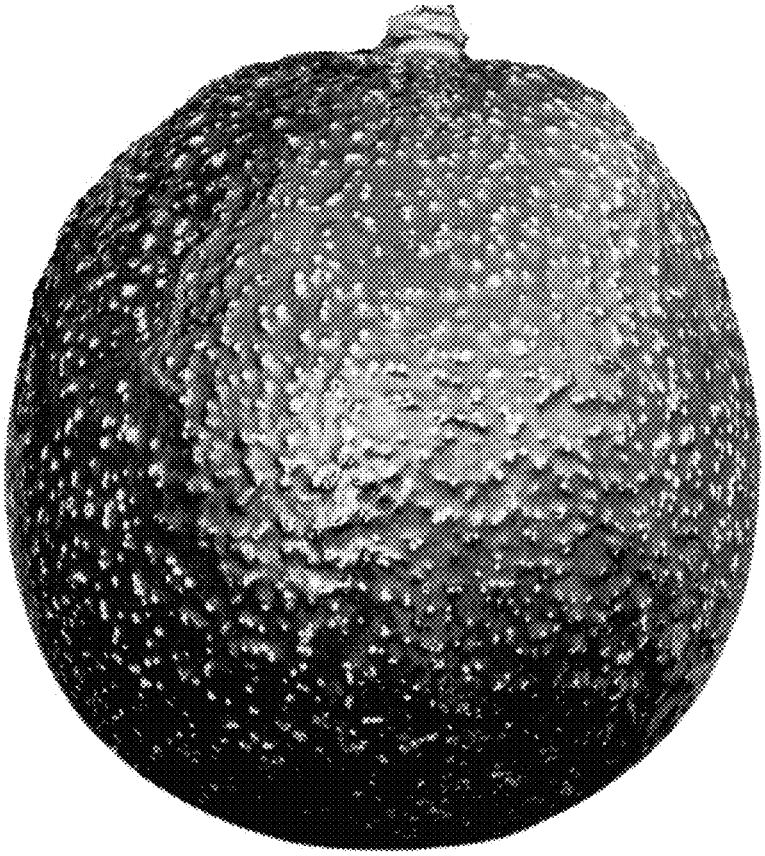

Latin name of the genus and species: *Persea americana* Mill.

Variety denomination: 'GUACACADO'.

BACKGROUND OF THE INVENTION

'Guacacado' is a unique avocado tree variety discovered in a San Francisco Bay Area private garden, thriving in the San Francisco Bayfront fog belt climate zone approximately 200 miles north of California's primary avocado production region, demonstrating resilience to colder temperatures not typical for Guatemalan-type avocados. It originated from a seedling derived from open-pollinated breeding. The 'Guacacado' maternal parent was cut down prior to the selection being made and is no longer extant. The maternal parent tree was never professionally evaluated but is reported to have produced similarly large fruit with excellent eating qualities. The male contributing pollen parent of the 'Guacacado' variety is unknown.

The 'Guacacado' specimen tree was planted from a seed germinated approximately 15-20 years ago. During its lifetime, it only occasionally received supplemental irrigation beyond normal rainfall when surrounding potted plants were watered, simulating "semi-dry farming" conditions. It has received neither fertilizer nor mulch of any kind during its lifetime. Yet, despite the less-than-ideal growing conditions it has endured, 'Guacacado' has thrived, bearing thousands of pounds of fruit during its lifetime.

'Guacacado' was first asexually propagated in the Spring of 2020 by grafting budwood onto understock seedlings of the unpatented *Persea americana* 'Zutano' at the inventor's production nursery in Winters, California by both grafting budwood onto containerized seedling rootstocks and also by grafting budwood onto semi-mature in-ground trees. The inventor continued confidential, controlled propagation and evaluation of the variety since then confirming that the new variety is stable, and that the progeny are formed true to type.

There are assigned three "races" of avocado trees, each with unique attributes and geographic preferences. The first race is called "West Indian" (a likely misnomer) which typically produce very large but relatively bland avocados in lowland fully tropical climate zones and are thought to be native to lowland Central America before being spread by anthropogenic means to the West Indies prior to or closely coinciding with European contact. This race of avocado is too cold tender to successfully grow and reliably produce in the San Francisco Bay Area.

The second race, known as "Mexican," originates from the cooler, more northern latitudes of the Mexican highlands. Characterized by superior cold tolerance, Mexican avocados, including Mexican/Guatemalan hybrids, feature smaller fruit size and thinner skin, often assuming a pyriform shape. This race predominates in the San Francisco Bay Area and California's commercial growing zones, particularly through the pervasive presence of the Mexican/Guatemalan hybrid variety 'Hass' U.S. Plant Pat. No. 0,139.

'Guacacado' belongs to the third race of avocados, "Guatemalan." This race is characterized by large, usually round, or oblong spheroid fruit shapes with very thick skin and excellent eating qualities. Originating from the lower latitude, middle elevations of the Guatemalan highlands (typically ranging from 3000 to 7000 feet), Guatemalan avocados are more cold-hardy than their tropical West Indian counterparts but typically exhibit lower cold tolerance compared to Mexican types. Consequently, Guatemalan-type avocados are usually far more challenged than the Mexican types to grow and be productive in colder climate zones such as the San Francisco Bay Area which lies more than 200 miles north of the primary avocado production regions of California.

Noteworthy is the observation that when Guatemalan type avocado trees are found in the San Francisco Bay Area, they are typically found in the most frost-free regions. Paradoxically, these regions, characterized by cooler, maritime-dominated microclimates, often result in poor fruiting outcomes for Guatemalan types because they require substantial springtime heat to set fruit, a condition less readily met in these cooler microclimates. The 'Guacacado' variety bucks this pattern.

Adapted for Northern California's cool maritime climate, 'Guacacado' thrives in zone 17 Northern California Coastal Zone as drawn by Lane Publishing's Sunset Western Garden Book local climate classification system, and zone 10A on the more general 2023 USDA plant hardiness map, enduring seasonal frost, and occasional hard freezes to the mid 20s.

During the four-year observation period since its discovery, 'Guacacado' has consistently demonstrated its capacity to yield commercially significant quantities of fruit. Its unique ability to withstand freezing temperatures while maintaining high productivity within the cooler maritime coastal climate zone of Northern California is an anomaly for large purebred Guatemalan race trees. This exceptional adaptability positions 'Guacacado' as a variety suitable for cultivation not only within the coastal expanse of Northern California but also potentially extending northward beyond the state line border into the more favorable microclimates of southern coastal Oregon, significantly broadening the commercial avocado geographical growing zone far beyond the current and more southern confines of California's primary avocado production belt.

Currently, California's primary avocado production belt is limited to the intercoastal confines of the San Diego region to the south to the Morro Bay growing complex to the north. 'Guacacado' introduces a prospect for avocado cultivation in regions previously considered less conducive to such endeavors and potentially extending the North American avocado cultivation frontier much further northward.

The thick, durable skin, adorned with gold flecks, not only protects the flesh during shipping and allows for very efficient flesh extraction, but also offers marketing differentiation similar to the patented variety '3-29-5', U.S. Plant Pat. No. 14,239, marketed under the name "GEM". A supermarket in the UK has utilized the gold flecking of the variety '3-29-5' successfully for product differentiation marketing purposes. A similar marketing strategy could be employed for 'Guacacado'.

A fruit of comparable size, marketed under the brand 'Avozilla', unpatented, has found success in South Africa and Australia, commanding a premium price per pound when shipped to Europe. 'Guacacado' possesses the potential to capitalize on this specialized niche for large-sized novelty fruits within the local West Coast market and beyond.

The large size of 'Guacacado' provides potential time and labor savings to growers and packers during harvest operations. Pound for pound, less hand picking and packing repetitions are required to yield an equivalent weight of the dominant 'Hass' variety. Additionally, the exceptionally thick and durable skin of 'Guacacado' at 2 mm thick vs. 1.6 mm thick of 'Hass' offers an added layer of protection during picking, packing, and shipping operations, enhancing the overall resilience of the fruit and providing a timely enhancement to the current agricultural labor shortage in the United States in general and California in particular.

The voluminous flesh of a single 'Guacacado' avocado equates to that of approximately 3 to 6 average sized 'Hass' avocados, rendering it an efficient choice for guacamole production. Additionally, the efficiency of scooping out the fruit against the sturdy wall of its skin contrasts greatly to the more laborious task of extracting flesh from the comparatively more delicate and more easily breakable skin of the 'Hass' variety. Notably, the exceptionally thick and structural skin of 'Guacacado' resembles a protective shell which serves as a convenient and appealing vessel in which to serve guacamole. The author of this patent has never encountered an avocado of any type that has such a durable, thick skin as 'Guacacado'.

'Guacacado' addresses a notable gap in the California avocado market, providing a locally produced alternative during the seasonal scarcity from November to February when foreign imports, primarily of 'Hass' from Mexico, dominate the market. Domestically, there is a notable scarcity of California avocados available from November, marking the conclusion of the late-season Central Coast 'Hass' crop, through February, which represents the earliest harvest date for the more southerly, earlier-ripening San Diego County district 'Hass' crop. During this California production lull is precisely when 'Guacacado' is in its prime.

Moreover, the harvesting window of 'Guacacado' coincides with the winter holidays and, notably, the NFL Super Bowl which is by far the highest avocado demand point throughout the year. This timing alignment positions 'Guacacado' as a novelty fruit for holiday gifting and game day guacamole feasting. Its late seasonality in Coastal Northern California not only offers a local option to meet seasonal market demand but also contributes to economic and environmental sustainability by reducing the reliance on foreign avocado imports.

SUMMARY OF THE INVENTION

The cultivar 'GUACACADO' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'GUACACADO' as a new and distinct *Persea americana* cultivar:

1. Cold hardy.
2. Exceptionally large fruit size ranging from 20 to 48 ounces.
3. Exceptionally thick, durable skin.
4. Fall to spring fruit maturation period.
5. Consistent, heavy fruit set in absence of nearby pollinator trees.
6. Consistent, heavy fruit set in cool climate zone.

COMPARISONS TO PARENT VARIETIES

An accurate record of the seed parent characteristics is not available for comparison.

The pollen parent is unidentified.

BRIEF DESCRIPTION OF THE PHOTOGRAPHS

The accompanying photographic illustration shows typical samples of fruit on 15 to 20-year-old specimens of the new variety, in color as nearly true as it is reasonably possible to make in a color illustration of this character. Plants were grown in the San Francisco Bay area in California. Colors in the photograph may differ from the color values cited in the detailed botanical description below, which accurately describes the colors of the new variety.

FIG. 1 Freshly harvested 'Guacacado' avocado fruit showing general shape, skin color and lenticel golden speckles.

Figure 2:
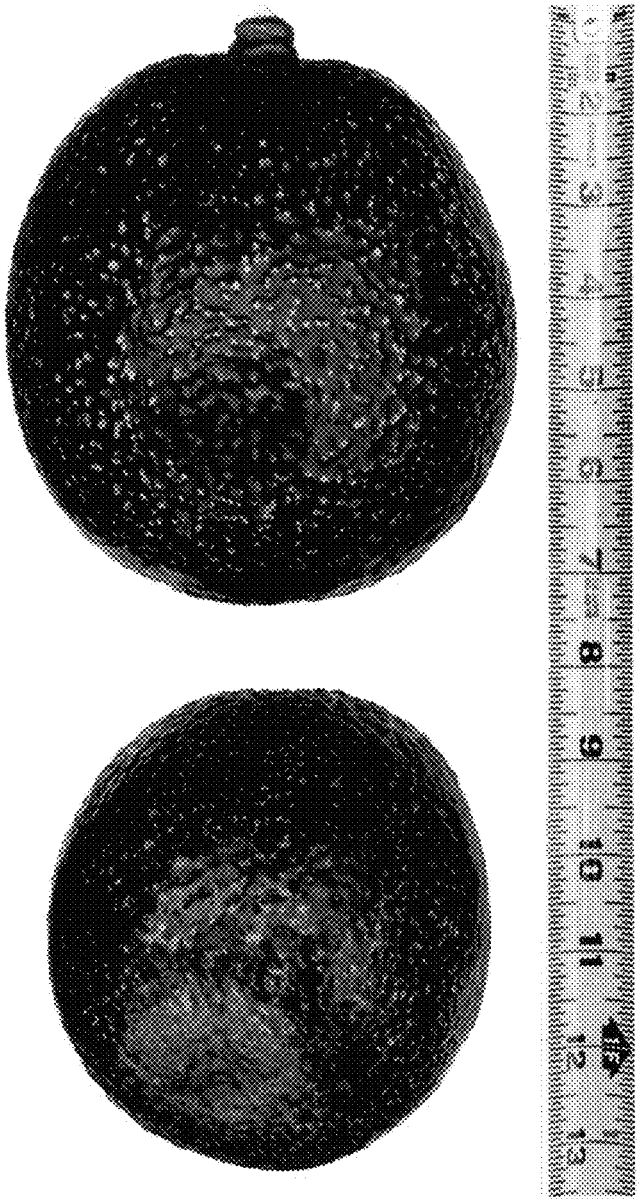

FIG. 2 Showing average typical fruit size range of variety from large to small. Fruit is generally 20-32 ounces (566-907 grams) in weight with fruit as large as 48 ounces (1361 grams) occurring.

Figure 3:
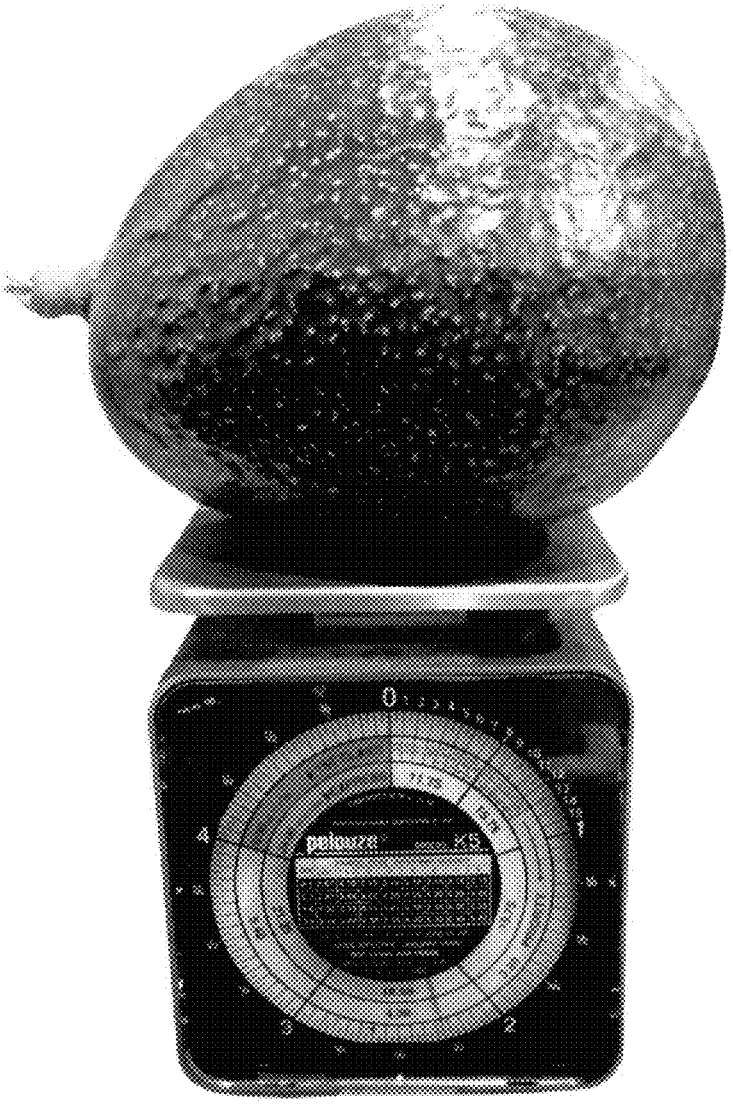

FIG. 3 Typical large sized 'Guacacado' avocado weighing 36.5 ounces (1035 grams).

Figure 4:
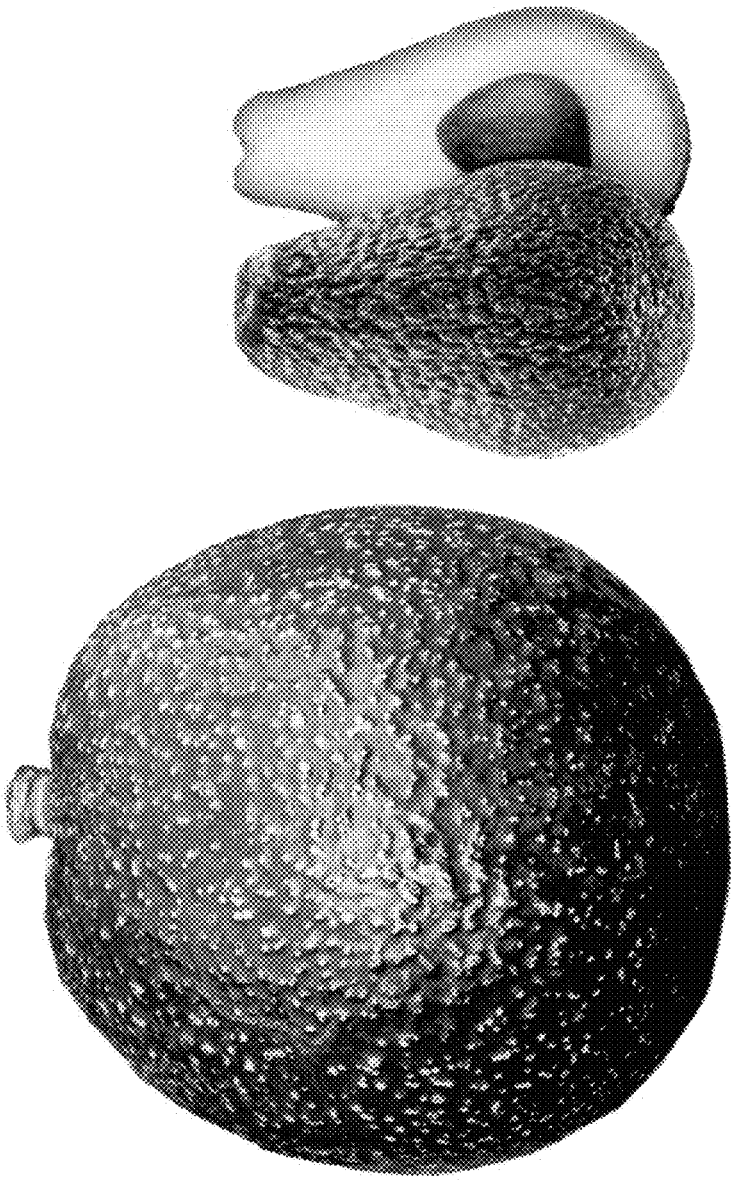

FIG. 4 Visual size comparison of freshly harvested typical 'Guacacado' avocado with typical 'Hass' avocado.

Figure 5:
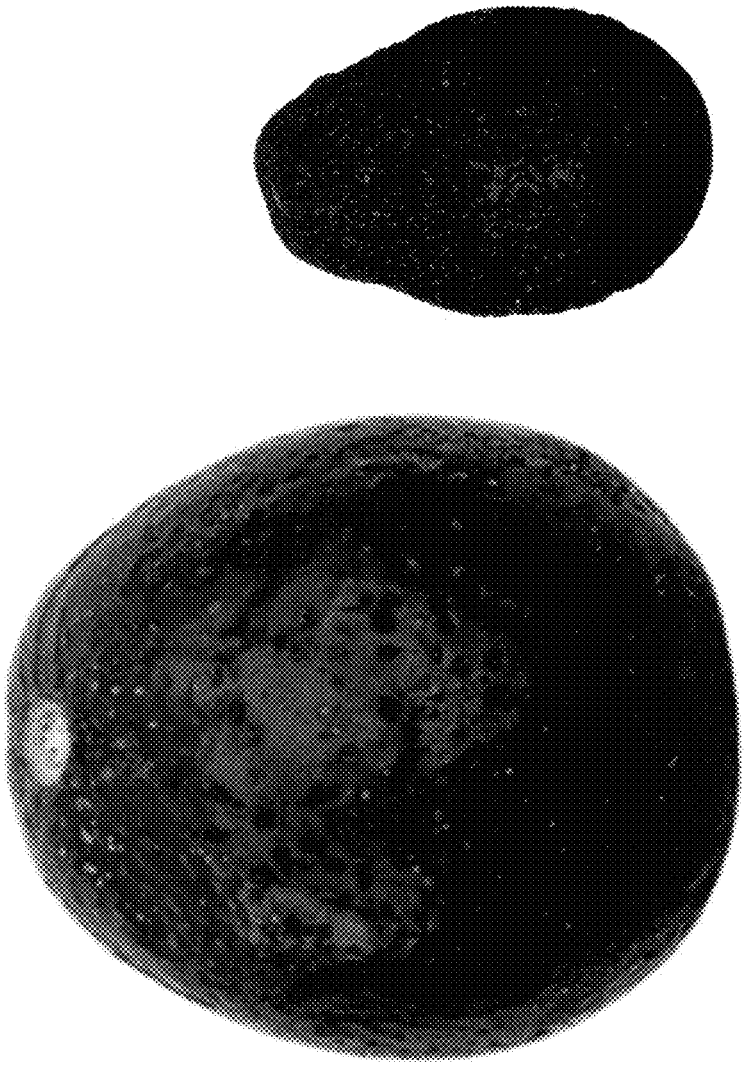

FIG. 5 Visual size and color comparison of ripe and ready-to-eat typical 'Guacacado' avocado with typical 'Hass' avocado, both turning to a dark green to near black color when fully ripened.

Figure 6:
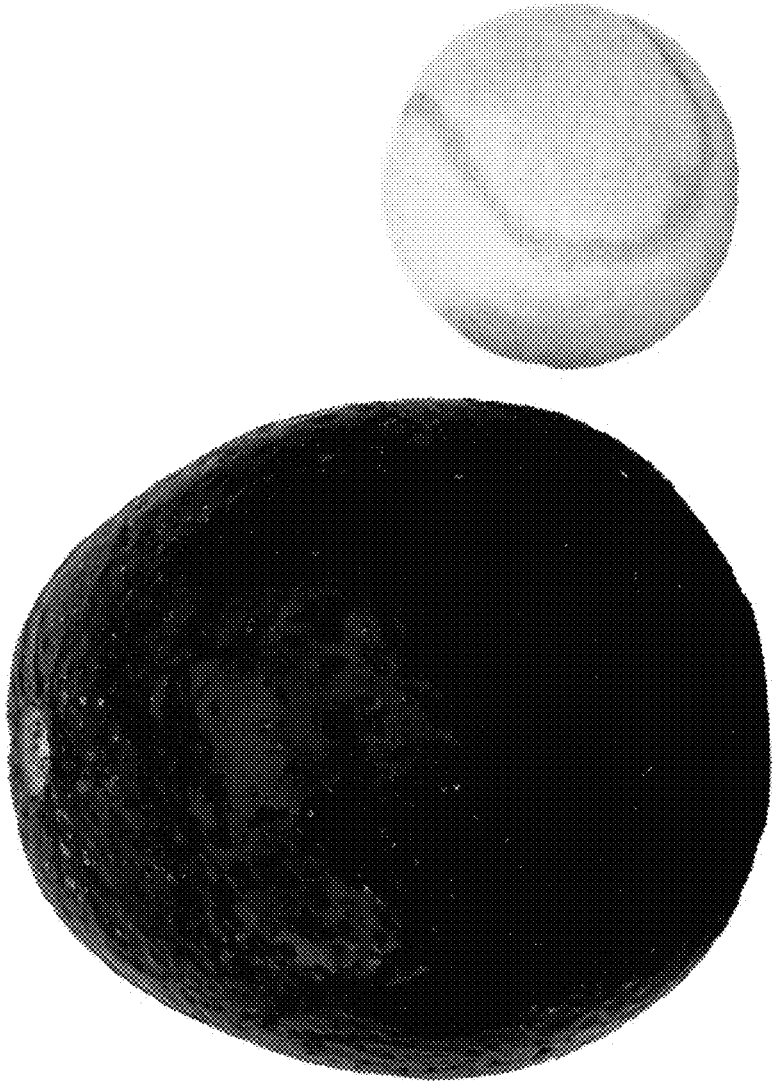

FIG. 6 Size comparison of typical ripe and ready-to-eat 'Guacacado' avocado with a standard tennis ball.

Figure 7:
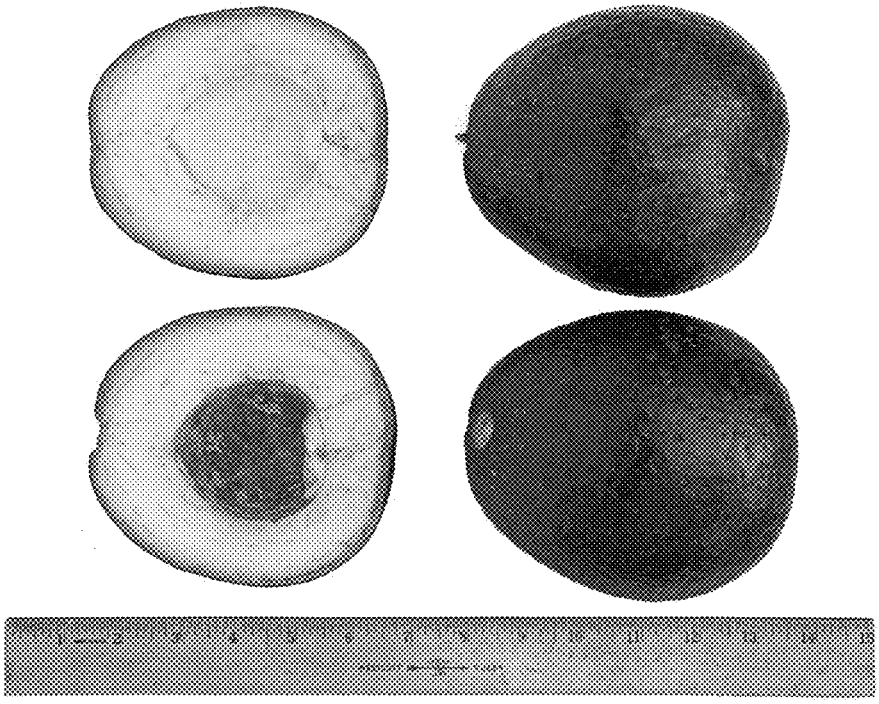

FIG. 7 Typical size and shape of the 'Guacacado' avocado showing external skin and half cross-section with seed.

Figure 8:
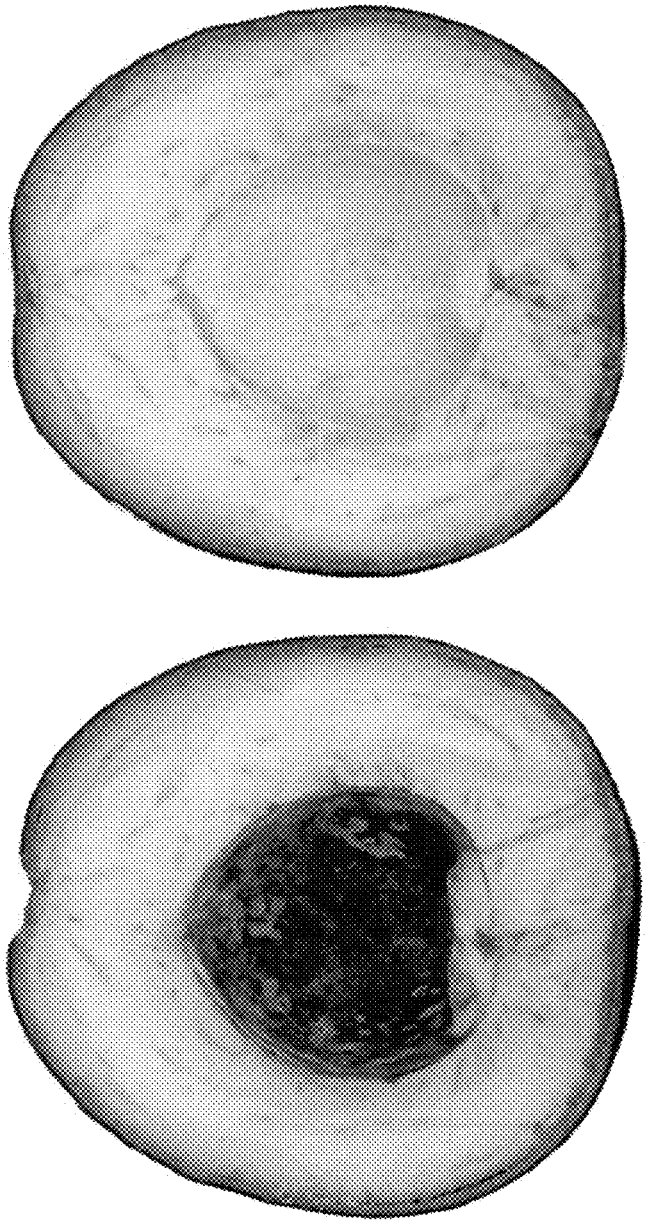

FIG. 8 Cross section of 'Guacacado'.

Figure 9:
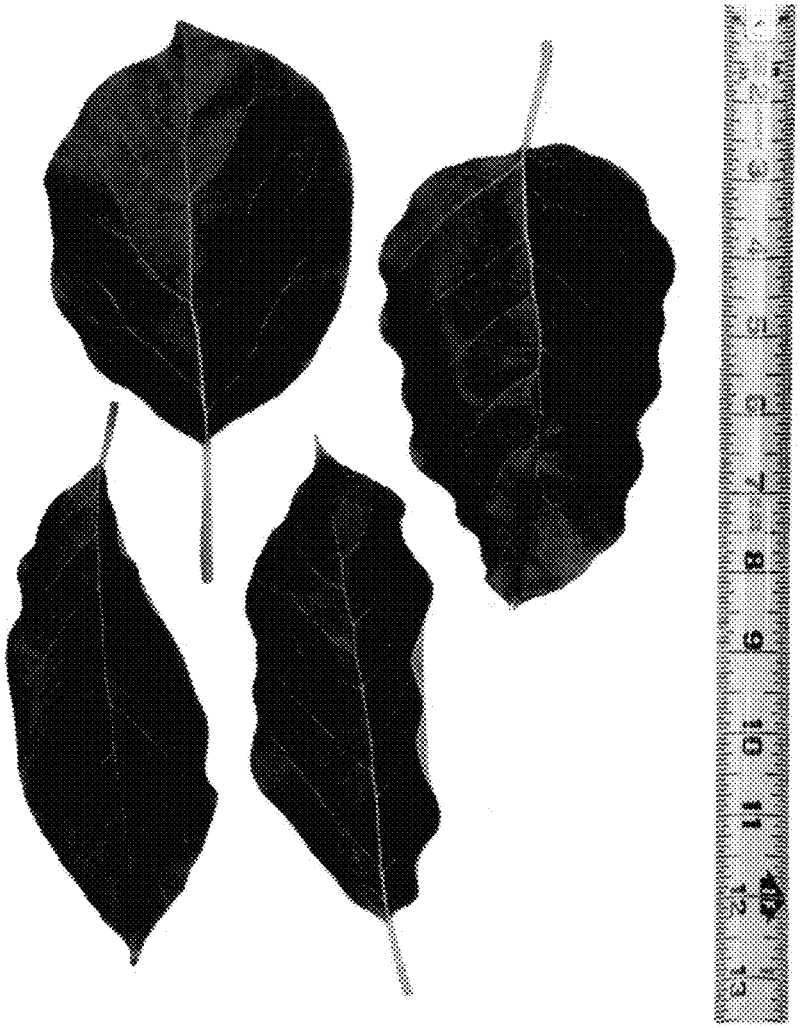

FIG. 9 Typical range of leaf shapes and sizes from 'Guacacado' variety.

Figure 10:
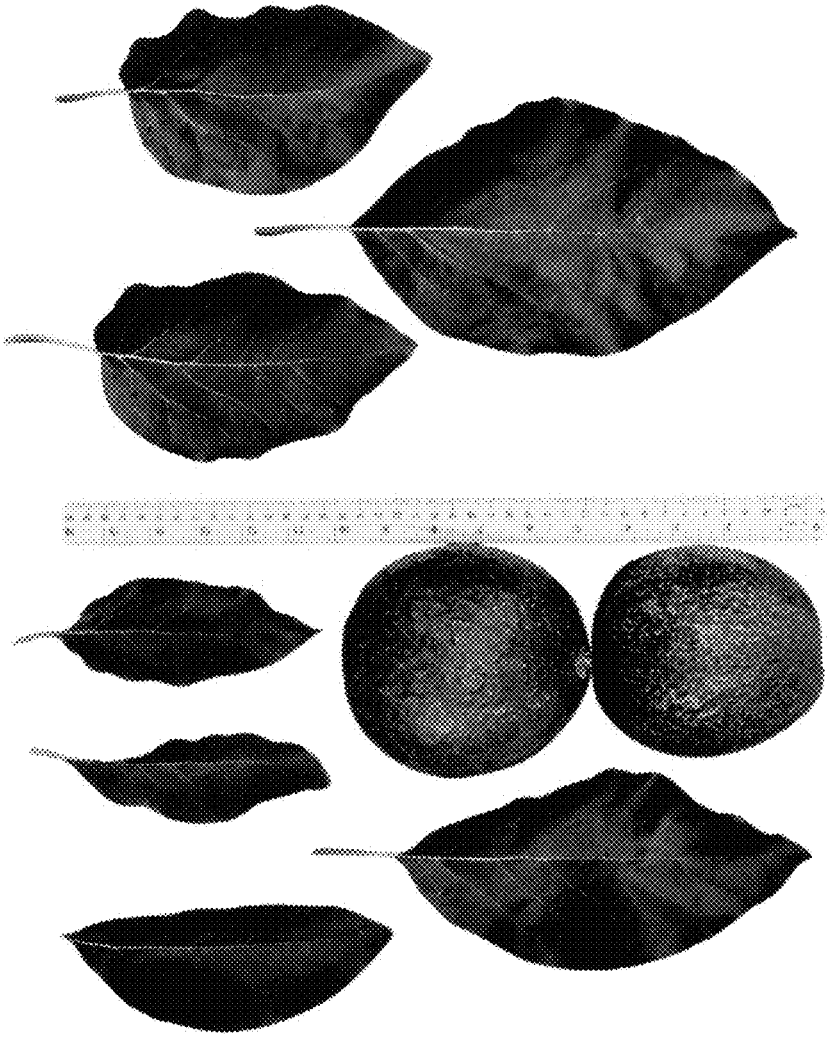

FIG. 10 Typical range of leaf shapes and sizes from 'Guacacado' variety side by side with fruit.

Figure 11:
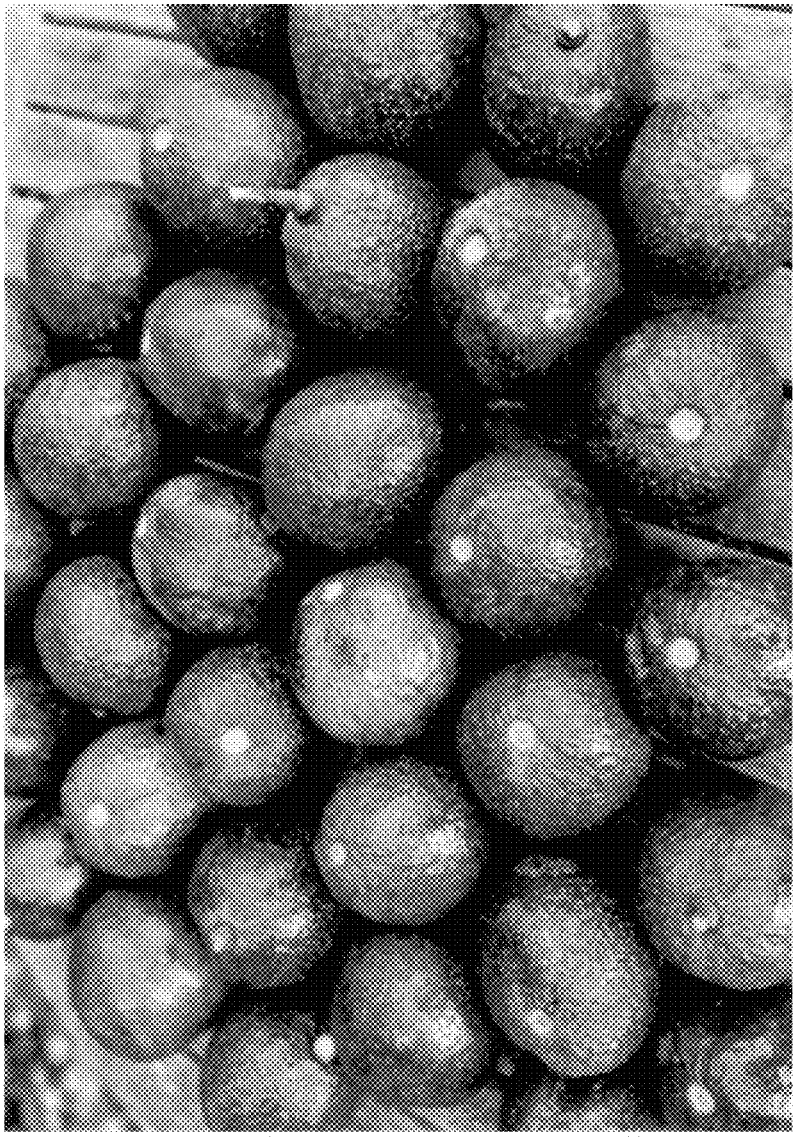

FIG. 11 'Guacacado' avocados laid out in masse.

Figure 12:
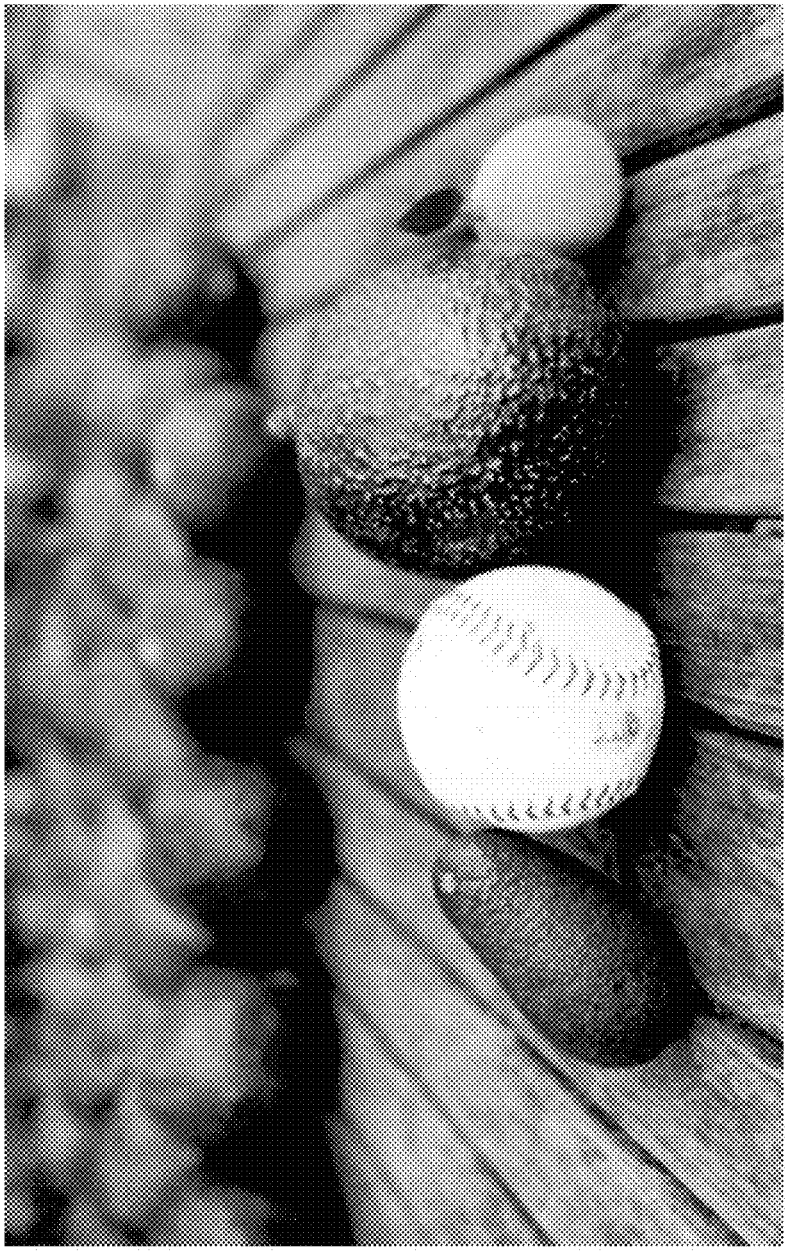

FIG. 12 Size comparison of typical 'Hass' style avocado with 'Guacacado' avocado and softball and lemon for comparison.

Figure 13:
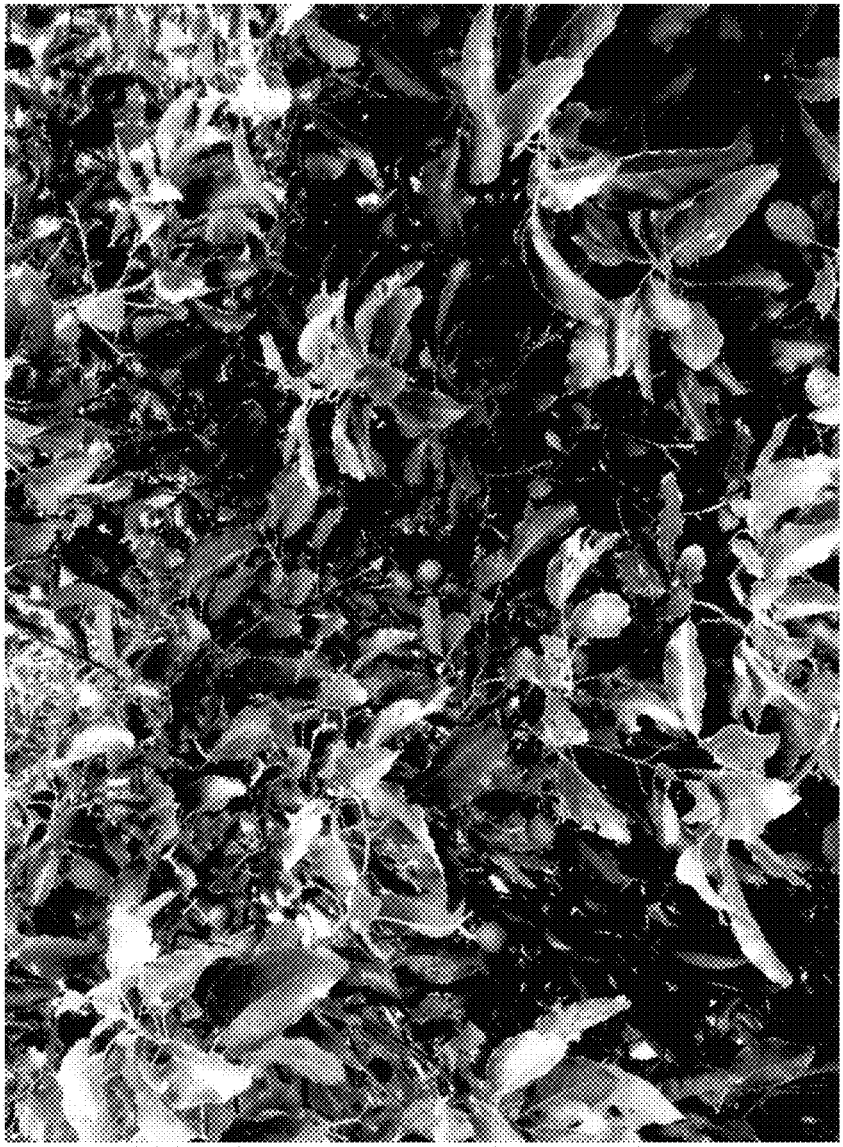

FIG. 13 This photograph taken in August shows typical foliage of the variety as well as 4 month old fruit hanging on the tree from the preceding Spring's flowering event. This fruit will need at least 12 more months hang time on the tree to fully size up and mature to be ready to harvest and eat. The much larger previous year's fruit is hidden deeper in the tree and covered by subsequent foliage push.

Figure 14:
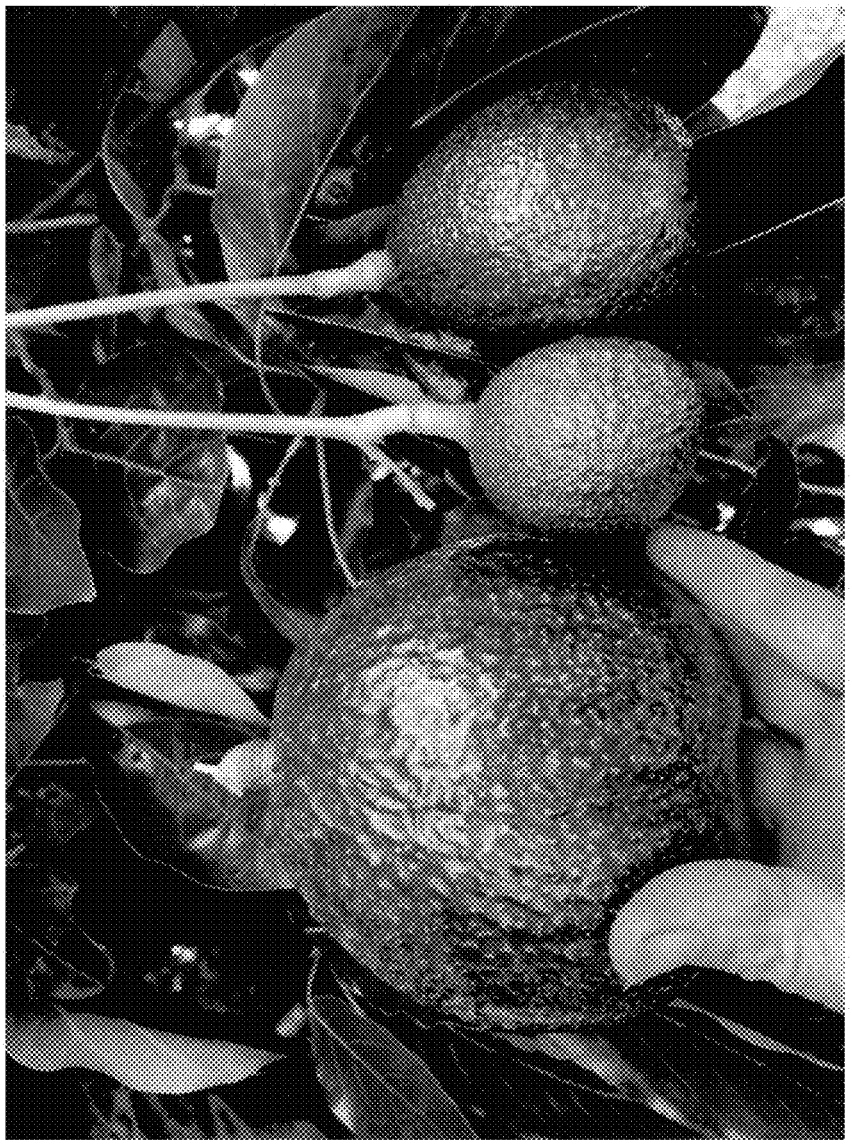

FIG. 14 This photograph taken in August shows a nearly mature 14-15-month-old fruit from the previous year's spring flowering side by side with immature 3-4-month-old fruit.

Figure 15:
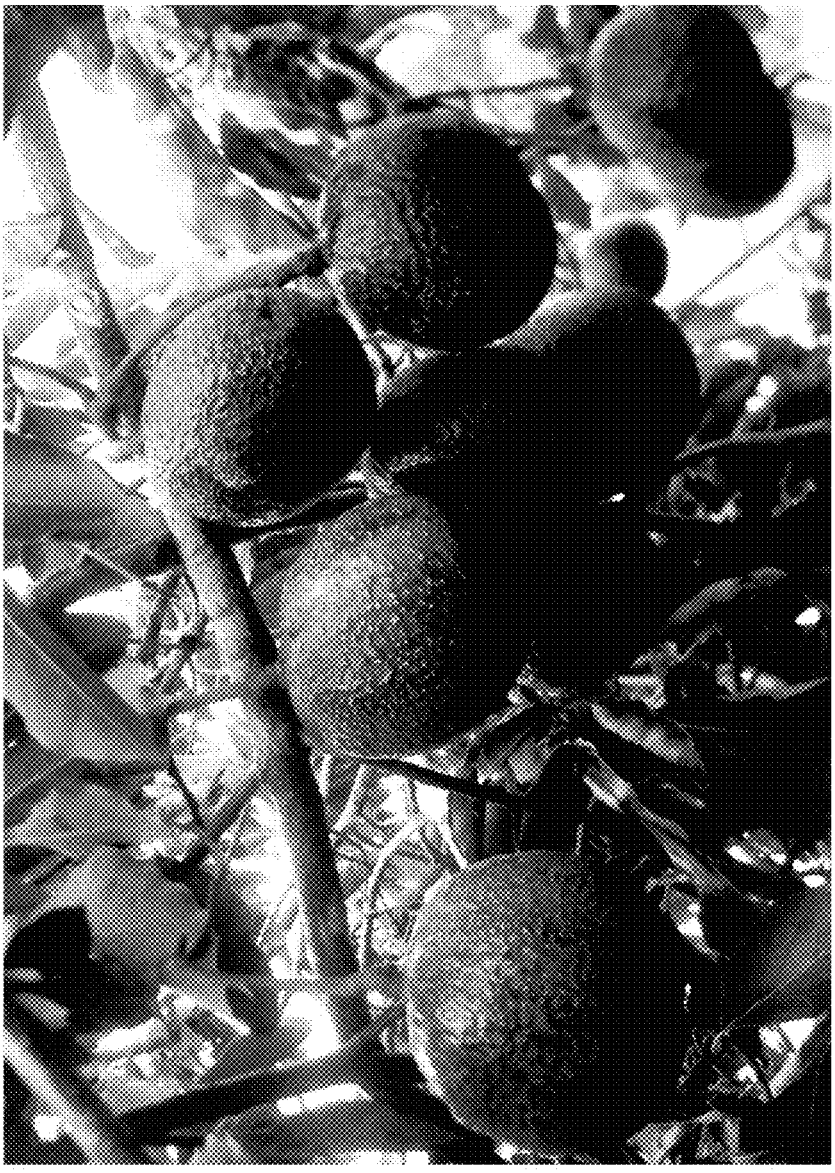

FIG. 15 'Guacacado' avocados ready to harvest on tree.

Figure 16:
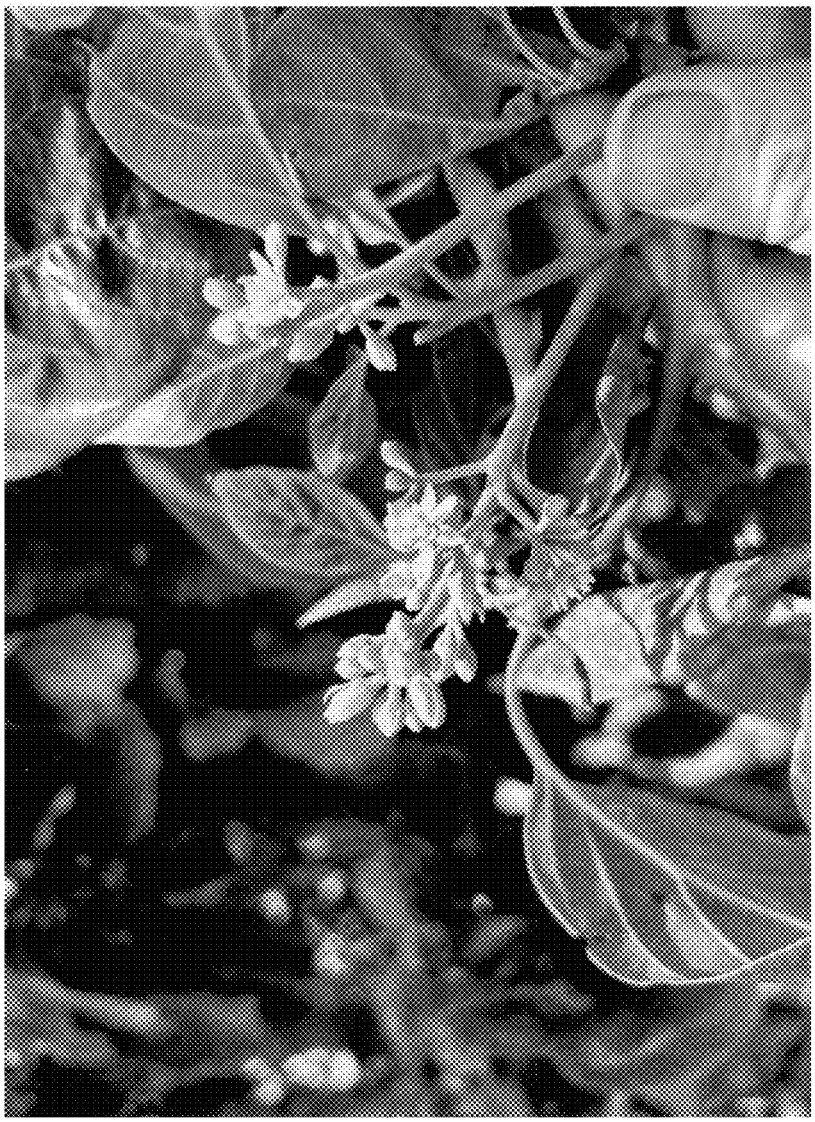

FIG. 16 'Guacacado' avocado flower set.

DETAILED BOTANICAL DESCRIPTION

The following is a detailed description of the new 'Guacacado' variety. As of this writing, the tree is approximately 15 to 20 years of age from seed. The structure, form and habit of the tree are similar in many regards to other Guatemalan or mixed-race Guatemalan/Mexican avocado trees so the focus of the descriptions below are mainly for defining differences. Colors are as defined by The Royal Horticultural Society Color Chart (2007).

Botanical classification: *Persea americana* Mill. 'GUACACADO'.

Tree:

*Growth habit*.—'Guacacado' is a rather open structured tree that is taller than wide at 25' tall by 20' wide as of the writing of this document. As the specimen tree is seedling grown, as such it would naturally have a propensity to get larger than a typical grafted tree. Overall growth habit of the tree is upright with semi-drooping branching ends.

*Main stem bark*.—Near RHS Greyed-Green 197D.

*Branch color*.—The color of the one-year-old branch is RHS Light Yellowish Green N144D, the most recent fully formed flush is also RHS Light Yellowish Green N144D.

*Smoothness*.—The bark of a one-year-old branch is smooth and typical of the species.

Foliage:

Leaf:

*New leaf flush color*.—Like many other avocado varieties, the young leaves of 'Guacacado' emerge in varying tones of coppery red with an average hue of RHS Greenish Reddish Orange 174D with a glossy surface.

Mature leaf:

*Shape*.—Leaf shape is elliptical to slightly ovate with acute tips. Leaf bases range from acute to slightly obtuse.

*Attitude*.—Upwards and outwards attitude of leaf to branch, similar in this regard to the common variety 'Fuerte', unpatented.

*Length*.—Leaf length is highly variable but generally ranges from 15-25 cm.

*Width*.—Leaf width is highly variable but generally ranges from 4.5-13 cm.

*Color*.—RHS Green 131A on the upper surface and near RHS Green 138B on the under surface.

*Venation*.—Pinnate and near RHS Yellow-Green 150D in color. Venation on upper surface is level with the rest of leaf surface.

*Margin*.—Entire and wavy like the variety 'Fuerte'.

*Anise aroma*.—Anise fragrance has not been detected in the stems or leaf.

Flower:

*Bud size*.—Approximately 5.1 mm in length and 3 mm in diameter.

*Bud shape*.—Ovoid.

*Bud color*.—Yellow-Green 152D.

*Sepals and petals*.—The sepals and petals of a newly, fully opened flower is borne in two whorls of three perianth lobes. The petal and sepal coloration is RHS Yellow-Green Group 154C.

*Stamen*.—Each normally formed flower possesses 9 stamens with four pollen chambers each and two nectar glands.

*Pistil*.—The single pistil with a slender style and small stigmatic surface has one carpel with one ovule. The ovary is superior.

*Pedicel*.—Approximately 4.3 mm in length and 0.6 mm in diameter possessing a slight hammer head with coloration of RHS Yellow-Green Group 150C.

*Number of flowers per inflorescence*.—Approximately 50-100 flowers per inflorescence.

*Pedicel*.—on average approximately 5 mm in length and 0.5 mm in diameter. The coloration is near RHS Yellow-Green Group 151B.

*Fragrance*.—Absent, no scent of anise.

*Bloom*.—Bloom period in Coastal SF Bay Area is generally April-June.

*Opening and pollination*.—Has predominantly behaved as a group "B" flower type, opening as female in the afternoon of the first day and closing in the evening or early night, followed by opening as male the morning of the second day. However, during many observations it was found that both male and female flowers were present at the same time. Situated as a standalone semi-isolated tree in a private garden with no other avocado trees within a 50-meter radius, and even then, sporadically so, it is likely that the tree relies heavily upon self-pollination for its ample fruit production. While all avocado trees are self-fertile to varying degree, 'Guacacado' particularly exemplifies robust self-fertility. In the absence of nearby avocado trees, and considering that the chief avocado pollinators are honeybees that typically operate within localized ranges, the 'Guacacado' tree seems to engage in self-pollination. This implies that male and female flowers are often open simultaneously, a phenomenon consistently observed by the inventor. Consequently, the tree can be confidently classified as a strong self-pollinator for an avocado tree.

Fruit:

*Skin color*.—Mature, harvest-ready hard fruit is overall Green 135A with flecks of Yellow-Green 150C. Ripened, ready to eat fruit varies in the dark green color range, including Green 139A and Yellow-Green 147A.

*Taste and quality*.—When ripe, taste is rich and buttery and considered by all who have tasted it to be of high quality.

*Density*.—Medium density and firmness. Similar to 'Reed' (unpatented).

*Texture*.—Smooth and creamy, no noticeable fibers.

*Length*.—Generally ranges from 110 mm to 140 mm.

*Diameter*.—Generally ranges from 95 mm to 115 mm.

*Weight*.—Generally ranging from 550 gms to 1350 gms (20-48 ounces). Fruit weight is 50%-75% heavier on average than the variety 'Reed' which is considered an exceptionally large sized avocado.

*Seed/skin/flesh ratio by weight*.—Approximately 14:14:72. 14% seed (endocarp), 14% fruit skin (pericarp), and 72% flesh (mesocarp). This can be compared to 14:13:73 for the 'Hass' variety, 18:13:69 for the 'Gwen' (U.S. Plant Pat. No. 5,398) variety, and 19:16:65 for the 'Harvest' (U.S. Plant Pat. No. 14,238) variety.

*Shape*.—Spheroid, like 'Reed' but more asymmetrical.

*Fruit pedicel*.—Typical Guatemalan type, 12 to 18 cm in length with a fruit-sided imperfect conical taper at fruit attachment. Nailhead absent.

*Skin color of freshly harvested fruit*.—Mature, hard fruit is generally RHS Green Group 135A in coloration with gold flecks of RHS 150C adorning the skin like the patented variety '3-29-5'.

*Skin color of ripened and ready to eat fruit*.—Like the varieties 'Hass' and 'Lamb Hass' (U.S. Plant Pat. No. 9,753), 'Guacacado' fruit skin color turns to a dark green to near black color when fully ripened off the tree, and the presence of gold flecks is less apparent.

*Skin texture*.—Pebbled and medium rough.

*Skin structure*.—Extremely structural due to its thickness and pliability.

*Skin thickness*.—Approximately 2 mm on average. This can be compared to 1.6 mm for the 'Hass' variety which is considered a thick skin variety. 'Guacacado' has the thickest skin of any avocado the inventor has encountered. The skin is so thick it can almost be considered a shell.

*Skin separation*.—Separates readily and cleanly from the flesh when ripe.

*Presence of longitudinal ridges*.—Variable but often present and pronounced on the exterior of most fruit.

*Adherence of skin to flesh*.—None; separates readily and cleanly from the flesh when ripe.

*Main color of flesh*.—RHS Yellow-Green 140D.

*Fruit maturation*.—In the maritime climate of The San Francisco Bay Area, the 'Guacacado' avocado variety takes an exceptional time to fully mature from initial flowering. From the main lower set of April through June, the fruit will take 16 to 18 months to fully mature. This means fruit that is born on the tree in Spring of year one will become ready for harvest in the Fall of year two. And similar with other avocados, the oil content and taste richness increase with extended hang time on the tree. Mature fruit displays a darker and less shiny green hue than immature fruit.

*Fruit ripeness*.—Harvested fruit will take between 5-10 days to become ripe and thereby soften. To assess ripeness, apply gentle pressure to the skin and feel for "give" of the flesh inside. The more "give" in the flesh equates to more ripeness of the fruit. An even more accurate method of determining ripeness for thicker skinned avocados is "the toothpick test." By removing the button on the avocado's end and gently inserting a toothpick through the hole and into the flesh, ripeness can be fully ascertained. If the toothpick enters the flesh with gentle pressure, the avocado is ripe. Conversely, resistance indicates that the avocado requires more time on the counter for thorough ripening. This exacting method ensures an accurate assessment of 'Guacacado' ripeness, particularly valuable due to its unique skin thickness.

*Harvest period*.—The 'Guacacado' avocado exhibits its earliest maturing fruit approximately 16 to 18 months after flower pollination. Typically flowering from April to June, the fruit becomes harvest-mature by September to October of the following year. The tree exhibits "dual-cropping," holding one crop from the flowering of the previous year and a smaller-sized, immature crop from the current year's flowering for the subsequent year's harvest. Mature fruit can remain on the tree for 6 to 8 months, generally September through April.

Seed:

*Length*.—Approximately 4.6 cm on average.

*Width*.—Approximately 4.4 cm on average.

*Weight*.—Ranges from 60 to 75 gms.

*Shape*.—Globose to oblong globose, oblate spheroid.

*Shape* (*in cross section*).—Generally circular.

*Color of seed coat* (*fresh*).—RHS Brownish Orange 165B.

Other characteristics:

*Productivity and bearing*.—Throughout the professional evaluation period from 2020-2024, 'Guacacado' has demonstrated regular albeit somewhat alternate bearing characteristics, consistent with most other avocado cultivars. The year 2020 produced an exceptionally heavy crop, followed by a medium crop in 2021, a light crop in 2022, and notably heavy crop in 2023, with ample fruit still hanging on the tree as of this writing. A typical 'Guacacado' crop is 300-400 lbs of fruit per year per mature 20 year old tree. Like all avocados, annual yield will vary depending on climatological conditions present during flowering and fruiting period as well as availability of water and nutrients.

*Hardiness*.—'Guacacado' exhibits superb adaptability to the cool maritime climate of the SF Bay Area characterized by cool summer fog, seasonal frost and occasional hard freezes. The area's climate is designated zone 17 Northern California Coastal Zone in the Sunset Western Garden Book local climate classification system, and zone 10A on the more general 2023 USDA plant hardiness map. The specimen tree endured the freeze of 2007 as a much smaller tree without any visible damage according to the owner of the property. Notably, during this freeze event, the inventor's retail nursery, located less than 2 miles away within the same climate zone, experienced temperatures in the mid-20° F. range resulting in ground icing for several days and significant damage to freeze-sensitive plants, including avocado trees.

What is claimed is:

1. A new and distinct cultivar of Avocado tree named 'GUACACADO' as herein illustrated and described.

* * * * *